United States Patent [19]

Wuerfel

[11] Patent Number: 4,784,481
[45] Date of Patent: Nov. 15, 1988

[54] TRANSMITTED AND/OR INCIDENT LIGHT MICROSCOPE

[75] Inventor: Volker Wuerfel, Braunfels-Bonbaden, Fed. Rep. of Germany

[73] Assignee: Ernst Leitz Wetzlar GmbH, Wetzlar, Fed. Rep. of Germany

[21] Appl. No.: 897,759
[22] PCT Filed: Dec. 14, 1985
[86] PCT No.: PCT/DE85/00526
 § 371 Date: Aug. 13, 1986
 § 102(e) Date: Aug. 13, 1986
[87] PCT Pub. No.: WO86/03847
 PCT Pub. Date: Jul. 3, 1986

[30] Foreign Application Priority Data
 Dec. 22, 1984 [DE] Fed. Rep. of Germany ....... 3447128

[51] Int. Cl.$^4$ .............. G02B 21/26; G02B 21/20
[52] U.S. Cl. .................... 350/529; 350/514; 350/584; 350/589
[58] Field of Search ............ 350/529, 542, 582, 584, 350/589, 545, 514

[56] References Cited

U.S. PATENT DOCUMENTS

| | | |
|---|---|---|
| 1,973,066 | 9/1934 | Hauser et al. |
| 2,128,394 | 8/1938 | Berek. |
| 2,967,458 | 1/1961 | Stone, Jr. ............. 350/522 |
| 3,170,383 | 2/1965 | Hunt ................... 350/584 |
| 3,186,296 | 6/1965 | Erban .................. 350/528 |
| 3,848,150 | 12/1969 | Taoka et al. .......... 350/522 |
| 3,934,960 | 1/1976 | Ouchi et al. .......... 350/528 |
| 4,035,057 | 7/1977 | Klein .................. 350/522 |
| 4,128,944 | 12/1978 | Stanton ............... 33/180 R |
| 4,206,966 | 6/1980 | Tyson et al. .......... 350/529 |
| 4,248,498 | 2/1981 | Georges ............... 350/531 |
| 4,277,133 | 7/1981 | Staehle ............... 350/90 |
| 4,405,202 | 9/1983 | Kimball ............... 350/529 |
| 4,453,807 | 6/1984 | Faulkner et al. ....... 350/529 |
| 4,482,221 | 11/1984 | Emmel ................. 350/531 |

FOREIGN PATENT DOCUMENTS

| | | |
|---|---|---|
| 1109400 | 6/1961 | Fed. Rep. of Germany ...... 350/529 |
| 551673 | 4/1923 | France. |
| 396445 | 1/1966 | Switzerland. |
| 6087 | of 1912 | United Kingdom. |

Primary Examiner—John K. Corbin
Assistant Examiner—Ronald M. Kachmarik
Attorney, Agent, or Firm—Foley & Lardner, Schwartz, Jeffery, Schwaab, Mack, Blumenthal & Evans

[57] ABSTRACT

Transmitted-light and/or reflected-light microscope in closed or open vertical-frame stand design (1; 2) having a vertical object stage plane (5) and a horizontal optical microscope axis (7) which is perpendicular to the object stage (5). An alternative embodiment of the microscope casing comprises at least two vertical stand parts (11; 12) which are connected together by a stand plate (13) and—as seen by the observer (47)—are arranged one behind the other. A vertical object stage (5), to which the horizontally-extending optical axis (7) is perpendicular, is located between the two stand parts (11; 12). The angular deflection $\alpha$ between the vertical plane (63) and the object stage plane, and thus the angular deflection between the horizontal and the optical axis (7), can be up to 30° in both versions, according to the condition: $0° \leq \alpha \leq 30°$. In all embodiments, contamination-free handling and inspection of large-surface-area objects (6), particularly wafers, is achieved by the establishment of a laminar flow, acting in the region of the object. The observer (47) can carry out all necessary microexamination and handling functions from ergonomically-designed control panels (45, 55), which are all located outside of the critical object region on the instrument. The instrument system can be employed in fully-automated, in-process computer-controlled wafer inspection, measuring and handling lines as a central component.

30 Claims, 5 Drawing Sheets

TRANSMITTED AND/OR INCIDENT LIGHT MICROSCOPE

BACKGROUND OF THE INVENTION

The invention relates to a microscope for transmitted-light, reflected-light or combined transmitted-/reflected-light illumination for the investigation of large-surface-area objects, such as masks or wafers.

As optical instruments which serve, for example, for the inspection or the measurement of wafers or the alignment of mask and wafer, semiconductor microscopes and special-purpose mask comparison microscopes (double microscopes) are known which, in conventional fashion, possess one (or more) optical axis (axes) in the vertical position and one (or more) object stage(s) in the horizontal position.

The highly sensitive precision objects (wafers) with their currently known dimensions (up to 150 mm diameter) can admittedly be inspected or measured in an efficient manner using these known microscopic examination instruments. However, the wafer generation of the future will, inter alia, be characterized by an enlargement of the wafer diameter to 10 inches and more, and also by an increase in the object-specific structure density.

The following disadvantages and risks during wafer handling and investigation using the known types of semiconductor microscope arise from this:

the position of the large-surface-area wafer on the horizontal object stage leads to a greatly increased danger of breakage or scratching, particularly in its peripheral regions;

the operational possibilities are obstructed for the observer in an anti-ergonomic fashion;

the necessarily increased range of movement of the mechanical object stage in the horizontal x-y plane is limited or restricted by the microexamination position of the observer and by the instrument design;

the danger of contamination of the wafer surface increases in a dramatic and uncontrollable fashion, which becomes evident, for example, merely from the fact that even the very smallest dust particles, which can only be detected by microscopy, emanating from the body or from the clothing of the person impair the functions of a highly integrated circuit;

the area space requirement of a known semiconductor microscope to be equipped for such objects or of an entire inspection station to be equipped for such objects increases correspondingly;

stability problems caused by the design arise for the microscope.

SUMMARY OF THE INVENTION

The object of the present invention is to provide a reflected-light, transmitted-light or reflected-light and transmitted-light microscope, equipped, in particular, for the investigation of large-surface-area, two-dimensional objects, which permits the observer, in the microexamination position, ergonomically ideal operating manipulations on the instrument, additionally, allows contamination-free inspection and transport of the object, and, finally, can be equipped, in a stable, space-saving design, even for extremely large object surfaces or can be used as an integral module within a modern wafer-production line.

In the case of a microscope of the type mentioned initially, this object is achieved, on the one hand, in that it has the design features as listed below: the microscope casing comprises a frame stand of open or closed design having, as seen by the observer, one front frame stand part and one rear frame stand part; an object stage for receiving or holding preferably large-surface-area objects is located between the front and the rear frame stand parts; the microscope's optical axis, which is oriented with its section, on the object side, perpendicular to the object stage plane, forms a discrete angle, between 0° and 30°, but preferably 0°, with the horizontal, so that the following is valid: $0° \leq \alpha \leq 30°$.

The object is achieved on the other hand in that the microscope of the type initially mentioned has the design features listed below: the microscope casing comprises at least two stand parts, which are preferably connected to one another by at least one common stand plate; the stand parts, from the view of the observer, are located one behind the other; an object stage for receiving or holding preferably large-surface-area objects is located between the front and the rear stand part(s); the microscope's optical axis, which is oriented with its section, on the object side, perpendicular to the object stage plane, forms a discrete angle, between 0° and 30°, but preferably 0°, with the horizontal, so that the following is valid: $0° = \alpha = 30°$. Further forms of the present invention are described hereinafter.

BRIEF DESCRIPTION OF THE DRAWINGS

Exemplary embodiments of the present invention are represented schematically in the drawings, in which:

FIG. 1b shows the plan view of the microscope represented in FIG. 1a;

DETAILED DESCRIPTION OF PREFERRED EMBODIMENTS

Figure 1A:
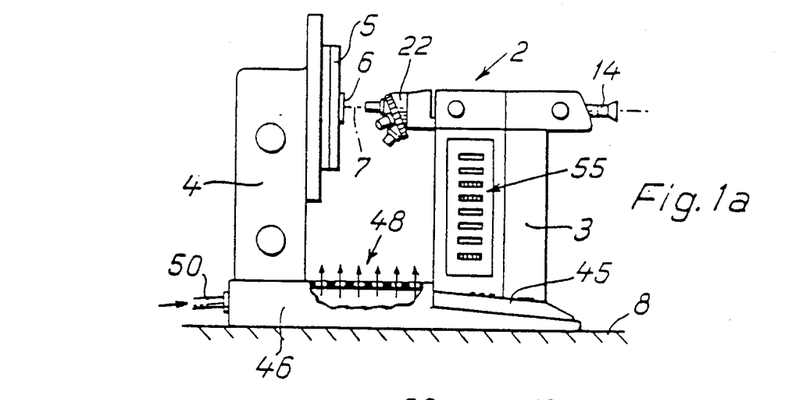
FIG. 1a shows a side view of a vertical-stage microscope which is constructed in an open vertical-frame stand design.
Figure 1B:
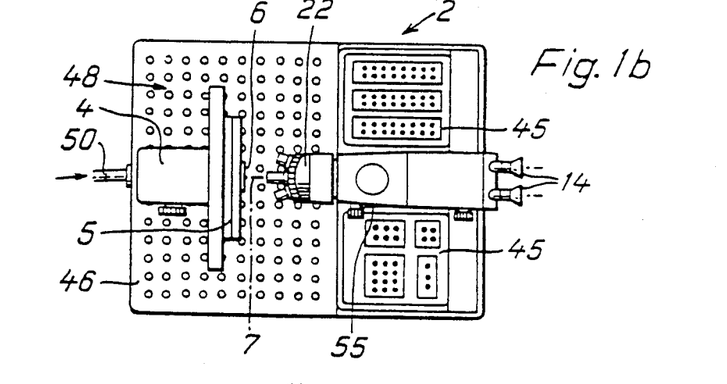
Figure 1C:
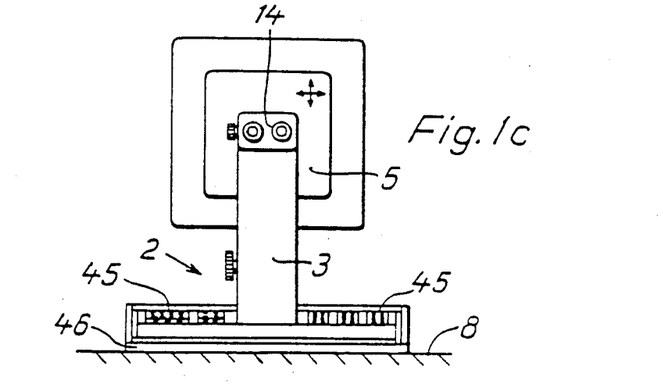
FIG. 1c shows the front view of the microscope represented in FIGS. 1a and 1b.

A first embodiment of the present invention is represented in FIGS. 1a-1c. The microscope casing comprises a front vertical frame stand part 3 and a rear vertical frame stand part 4, which are both mounted rigidly on a common base plate 46 or are constructed in a one-piece design. The two frame stand parts 3 and 4 and the base plate 46 together form an "open" frame stand 2, in contrast to the "closed" frame stand 1 represented in FIG. 2. The open frame stand 2 is constructed in a vertical design, that is to say its longitudinal section plane lies in the plane of the drawing and is perpendicular to a horizontal supporting surface 8. The front frame stand part 3 carries an observation unit, which contains a binocular eyepiece 14 and a revolving objective nosepiece 22; the rear frame stand part 4 carries an object stage 5, for example a rotating mechanical stage for receiving an object 6. In the illustrated embodiment, the optical axis of the microscope extends horizontally and the object stage plane is perpendicular to the surface 8. Since exemplary embodiments are also described below which have optical axis sections which deviate from the horizontal, it should be noted at this point that in what follows all that is important is the positional characterization of that portion of the optical axis of the microscope which extends from the objective, positioned in the operational position, of the revolving objective nosepiece 22 to the object 6 or to the object stage 5.

Although a reflected-light arrangement is shown in the illustrated embodiment, illumination devices (light source, condenser optics, diaphragms) which are known per se can also be present in the rear frame stand part 4 to produce a combined reflected-light/transmitted-light illumination beam path.

Similarly, for the sake of simplicity, attachment faces for external lamp housings or other modules, for special purposes, which are conventional in microscope technology have not been illustrated. An important instrument design feature is the control panel 55, which is located in the lateral region of the front frame stand part 3 and from which many of the possible operational functions can be initiated. Of course, this control panel can also be arranged directly on the front side, facing the observer, of the frame stand part 3.

Further operational functions can be initiated from the console 45. It should be emphasized that no operations need be carried out by the observer in the proximity of the object. The changeover of the objective, the mechanical stage positioning, the focusing, the change of the type of illumination, the attachment of external modules or the exchange of internal modules, and even the replacement of the object can be carried out automatically. The vertical orientation of the object stage greatly limits the danger of deposition of object-contaminating airborne particles from the air in the room. As an additional measure for the exclusion of dust particles, a permanent "laminar flow" is provided in the transverse direction to the planar object, as indicated by the air inlet aperture 50 and the air flow apertures 48 present in the upper region of the base plate 46, cf. their matrix arrangement in FIG. 1b. It is also possible to reverse the throughflow device, in other words to create a through-suction device.

Figure 9:
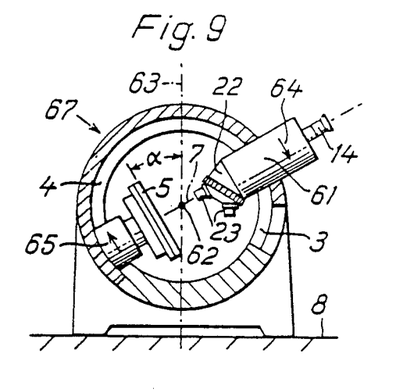
FIG. 9 shows, in side view, a highly schematicized third special version of a vertical-cylinder frame stand in closed design having a variable angular position of the object stage plane.

Although a precise vertical orientation of the object stage plane, and thus of the object 6, for example a silicon wafer of diameter 200 mm, offers the least possible landing area to a permanently threatening sprinkling of dust particles and is thus to be favored, it is also possible to tilt the object stage 5 through a certain angle $\alpha$ into an oblique position in the manner of a music stand. The angle $\alpha$ should, in this case, not exceed the range $0° = \alpha = 30°$. Here, a tilting of the object stage out of the vertical position through an angle $\alpha_1$ corresponds to a tilting of the portion 7 of the optical axis of the microscope oriented toward the object to be viewed, out of the horizontal position through precisely this angle $\alpha_1$, since the axis portion 7 oriented toward the object, should always be perpendicular to the object 6. The means provided for this are not represented in FIGS. 1a-1c, or in the majority of the Figures to be described further below. These means can be created by means of appropriate mechanical translation and coupling means. Static ("frozen") tilted versions are shown, for example, in FIGS. 4-6, 11 and 12; FIG. 9 shows a dynamic tilted version.

Figure 2:
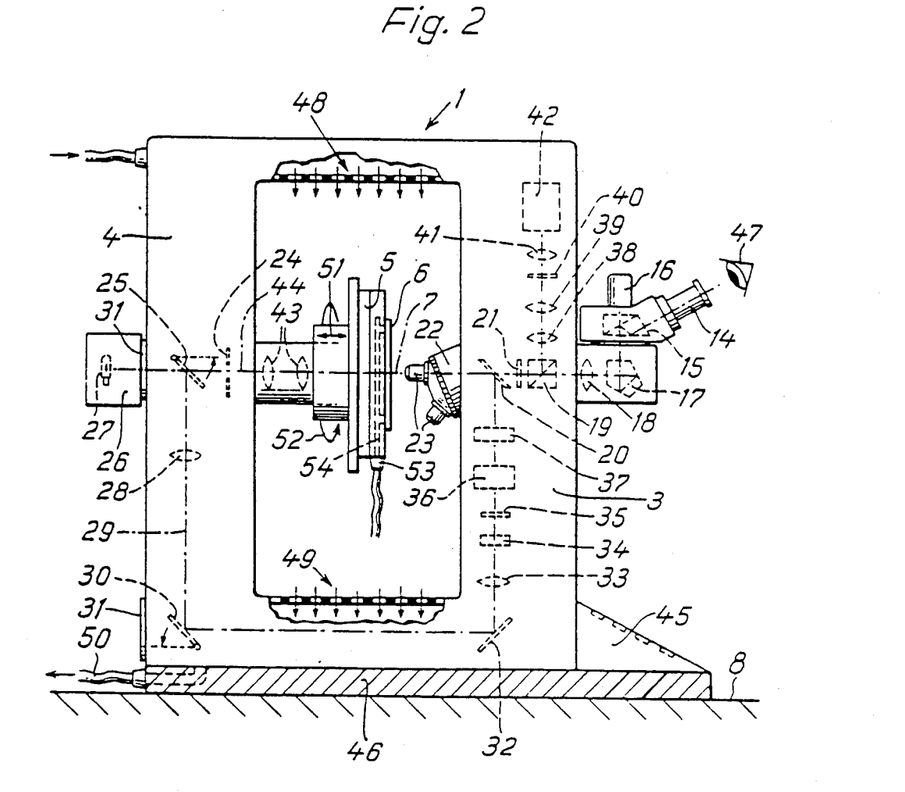
FIG. 2 shows a side view of a vertical-stage microscope which is constructed in a closed vertical-frame stand design with rectangular longitudinal section, with a representation of several of the optical, mechanical and electronic components or modules which are present in the partial beam paths.

FIG. 2 shows a side view (longitudinal section) of a second embodiment of the present invention. The vertical frame stand 1 is "closed"; the front frame stand part 3 and the rear frame stand part 4 are connected via a frame stand base part and a frame stand cover plate. The rectangular frame is constructed in one piece. The region of the base plate 46 is extended towards the observer and carries the console 45. A laminar-flow object flushing device is characterized, in the region of the cover plate, by the air flow apertures 48 and, in the region of the upper part of the base plate, by the air suction apertures 49—in each case again in a matrix arrangement—and also by the tube 50. The vertical frame stand 1 contains, in the region of its vertical stand parts 3 and 4, and specifically on their respective sides facing away from the object 5, flange attachment faces 31 for attaching external modules, for example a lamphousing 26 or a structural member, containing optical components 17, 18, onto which a binocular tube can be placed which can possess, for example, a photo connector 16.

The optical beam path is represented in FIG. 2 as a transmitted-light illumination beam path. From a light source 27 in the lamp housing 26, the reflected-light illumination beam 29 reaches the objective 23, acting as a condenser, as a bent beam path via a hinged mirror 25, after first passing through a reflected light illumination optic 28, then a deflection element 30, which can be a rotatably mounted deflection prism, but in the present case is represented as a second hinged mirror, then a further deflection element 32, subsequently a second reflected-light illumination optic 33, then an interference contrast device (polarizer) 34, further a full-wave plate, subsequently an autofocus system and diaphragms arranged after this, and finally a deflecting element which is provided with a partially transparent beam-splitting surface 20, and from there it reaches the reflected-light object, for example a wafer. The image-forming and/or measurement ray bundle emanating from the object proceeds through the objective 33 and, after passing through the beam-splitting surface 20 and an analyzer 21, onto a beam splitter cube 19, from where a part of the beam bundle is taken off for measurement, this part being guided to, for example, a modularly arranged intensity or spectral measurement instrument after passing through a tube lens 38, a further optic 39, a dimension- or angle-measuring system 40 which can be engaged if desired and a further optic 41.

The part of the image-forming beam bundle which passes through the beam splitter cube 19 is guided, via a tube lens 18 and a deflection prism 17, to a deflection/splitter prism 15, from where the actual observation part of the beam bundle is deflected into the eyepiece or eyepieces 14, and a recording part of the beam bundle is deflected into a photo connector 16.

As shown in FIG. 2, the portion of optical axis 7 oriented toward the object 6 to be viewed is horizontal, i.e. forms an angle of 0° with the horizontal, whereas the portion of optical axis 7 passing through eyepiece 14 forms an angle with the horizontal.

The method whereby the transmitted-light illumination beam path is created is that the illumination beam bundle 44 emanating from the light source 27, when the hinged mirror 25 is in the position where it is swung out of the beam path, passes initially through a field diaphragm 24 and then through a transmitted-light illumination optic 43, in order to penetrate subsequently a—for example large-surface-area—transmitted-light object 6.

The optical arrangements described and illustrated can be modified in a known manner. Thus, for example, a combined reflected-light/transmitted-light illumination can be achieved by an arrangement in which the transmitted-light illumination beam path last described proceeds from the lamp housing 26, while a reflected-light illumination beam path proceeds from a second lamp housing, not illustrated on the second flange face 31 in the region of the base plate, only the second hinged mirror 30 needing to be brought out of its working position.

The object stage 5 displays, in its upper plate region and represented schematically, vacuum or suction channels 54, which can be arranged, for example, radially and/or concentrically and which are connected to a vacuum-generating device via a vacuum tube 53. A two-dimensional precision object 6, which is highly sensitive to mechanical damage, can be held gently by means of the adjustable suction device. If desired magnetic or pneumatic clamping devices may be used to hold an object to be viewed on the object stage. In addition, locating lugs or linear or arcuate chamfers or clamping elements can be provided on the object stage surface as positioning, holding or adjustment aids.

The transport of the object onto the stage, particularly transport of a fragile large-format wafer, which is in the vertical position or in the slightly obliquely backward position, is achieved in a fashion which is gentle for the object, safe from contamination, freely accessible for the view of the observer and efficient with respect to the equipment. The rotatable object stage 5, cf. the circular arrow 52, can, in addition, be moved axially in the direction of the double arrow 51 so that the focus can be set. It is also possible to equip the objective revolving nosepiece 22 with an axial movement device. These translations can advantageously be carried out automatically by an integrated autofocus system 36. Above all, the rotation of the objective revolving nosepiece is performed by a motor, in order that no manual operations need be carried out in the vicinity of the object, which would necessarily lead to "microcontamination" of the completely structured integrated circuit (object).

FIGS. 3–6 show further versions of closed vertical-frame stand designs, in highly schematicized representation, which, regarding their fitting with optical members, can be equipped in principle analogously to the circumstances described in FIG. 2, that is to say they can in particular also possess reflected-light/transmitted-light illumination beam paths. In addition, they can, in principle, possess flange-mounting and attachment interfaces. In respect of their ergonomic design features (vertical control panels forwardly-displaced consoles; laminar-flow devices), that which has already been stated for FIGS. 1a–2 is also valid.

Figure 3:
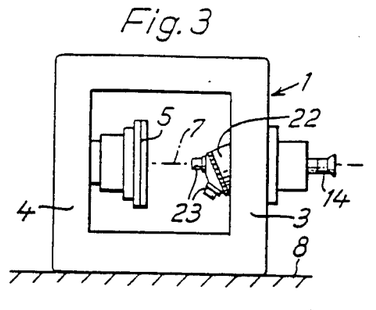
FIGS. 3-6 show highly schematicized side views of closed vertical-frame stand designs with differing geometry of the frame longitudinal section position of the object stage plane.

FIG. 3 shows a quadratic frame stand longitudinal section having a vertical object stage plane and a horizontal optical axis 7.

Figure 4:
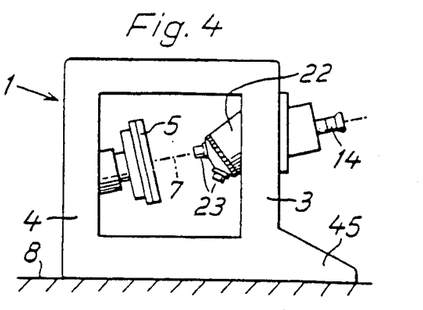

The representation in FIG. 4 differs from that in FIG. 3 only in that the object stage 5 possesses a fixed oblique backward orientation and the optical axis is deflected out of its horizontal orientation in corresponding fashion. Such an oblique orientation of the object (not represented) on the object stage 5 is expedient in those cases in which a permanent vacuum suction of the planar object is dispensed with, or when an object, for example a grid plate having a plurality of apertures, or a grid-structured planar object or one provided with through pores, is to be investigated. Locating strips or knobs or flat recesses, which are known per se, in the lower part of the object stage ensure a stable rest position of the object.

Figure 5:
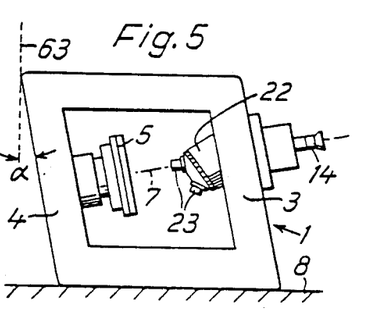

In FIG. 5, a parallelogram-shaped vertical-frame stand 1 is represented. The oblique orientation of the two frame stand parts 3 and 4—characterized by the angle a between represented by vertical line 63 the vertical plane and the surface of the rear frame stand part 4—corresponds to that of the object stage 5.

Figure 6:
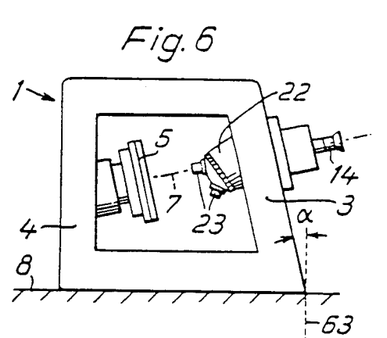

FIG. 6 shows a trapezoidal frame longitudinal section having an ergonomically advantageous oblique orientation of the front frame stand part. Although a vertical-frame stand has always been discussed hitherto, for reasons of simplicity, it should, however, be pointed out that the entire instrument must possess a frame width such that a compact, stable housing results which protects from external interferences and is fitted with all known optical microscope components.

Figure 20:
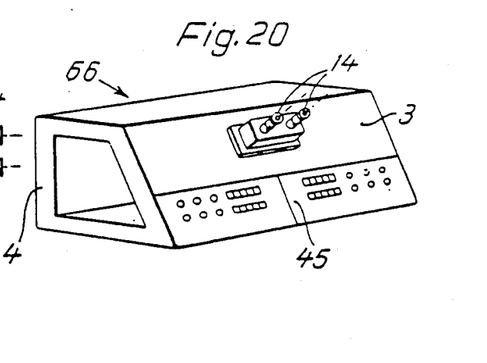
FIG. 20 shows a schematic representation of a closed frame stand version according to FIG. 6, but with extreme extension transverse to the optical axis in the fashion of a hollow section tunnel.

In FIG. 20, a hollow section design 66 is represented which can be derived from FIG. 6. The operating elements are, without exception, on or in the console 45 which is arranged at the lower front. If both sides of the housing transverse channel are partitioned off, a closed flow internal flow system or a selective protective gas atmosphere can be created if the air supply and discharge via the abovementioned apertures 48 and 49 is controlled. However, the tubular tunnel housing 66 extending transversely to the optical axis of the instrument can, above all, adopt a specific protective function during transport of the wafer to be examined onto and from the stage. All other disclosed geometries of the frame longitudinal section geometries can, in principle, also serve as hollow section cross sections. This is also true for the frame tunnel stand designs in the open type of construction which are to be described further below.

Figure 7:
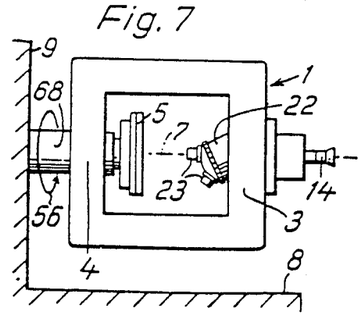
FIG. 7 shows, in side view, a highly schematicized first special version with a closed frame stand mounted so that it can rotate.

A special version is represented in FIG. 7. A closed frame stand 1 is penetrated, in the region of its rear frame stand part 4, by a cylindrical object stage holder 68, which is held, either rigidly or so that it can rotate, cf. the rotary arrow 56, on a vertical stop face 9—for example on a wall. The optical axis 7 of the microscope extends horizontally and is perpendicular to the vertical object stage plane. If the instrument parts 68 and/or 5 and/or 1, which are movable relative to one another, are appropriately mounted, coupled or decoupled, a rotation or a step-wise—for example by 60° in each case—rotation about the axis 7 can, for example, occur with a stationary object stage 5. On the other hand, it is also possible to rotate the frame stand 1 together with the object stage 5 in a corresponding fashion. These possibilities are extremely important, above all when the entire instrument represented in FIG. 7 is set up and employed, for example, in manner such that only the stop face 9 is present and the instrument, as a central inspection and measuring station, is surrounded by feed and removal lines, arranged in a star shape, which are arranged in a process line plane which is parallel to the face 9. By means of stepwise—for example microprocessor-controlled-rotation of the frame stand 1, a preselectable switch setting for the acceptance or delivery of a series of examination objects, particularly wafers, can be achieved. A vibration-free, robust suspension of the optical assemblies necessary for a microscope instrument is always assured in this case.

Figure 8:
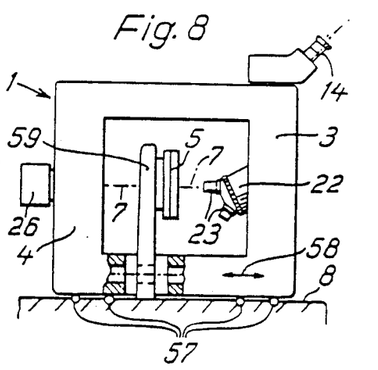
FIG. 8 shows, in side view, a highly schematicized second special version of a vertical-frame stand in closed design having fixed object stage coupling and having the possibility of translational motion of the entire frame.

In FIG. 8, another form of the movement of the vertical object stage 5 relative to the frame stand 1 is shown. The frame stand 1 is guided by bearings, cf. the reference number 57, on the horizontal ball surface 8 by means of its base frame part, while the holder for the object stage 5 is fixed rigidly on the surface 8. However, it is also possible to mount the object stage holder so that it can be moved axially.

FIG. 9 shows a further embodiment, according to the invention, in side view. This is a closed vertical-frame stand 67 which is circular in the longitudinal section (plane of the drawing). The circle center is denoted by the reference number 62, and the trace of an imaginary, vertical diametrical plane, which is perpendicular to the plane of the drawing, is denoted by 63. The right-hand half, facing the observer, of the circular arc corresponds to the front frame stand part 3. An observation module 61, comprising an eyepiece unit 14 and an objective unit 22, is secured to the said part in such a way that the portion of the optical axis 7 of the module 61 oriented toward the object to be viewed forms a discrete angle $\alpha$, which can be between 0° and 30°, with a horizontal line drawn through the center 62. In corresponding fashion, an optic stage 5 is secured to the rear frame stand part 4 in such a fashion that the optical axis 7 is always perpendicular to its plane. The two corresponding, diametrically mounted instrument assemblies 61 and 5 are advantageously secured to the stand 67 in such a fashion that the optical axis 7 extends horizontally. However, it is also possible to move both instrument assemblies 61 and 5 synchronously in opposite directions as indicated by the rotary arrows 64 and 65, through the aforementioned angle. In each case, it is ensured, by constructional measures, that the optical axis 7 extends through the center 62 of the system or that on axial movement of the object stage 5 in the direction of the objective revolving nosepiece 22 the center 62 comes to rest on the object surface and coincides with the point of intersection of the optical axis 7 with the object.

The advantages of this hollow cylinder frame stand version are: the setting of any desired optimal angle $\alpha$ which is dependent on the particular object and the specific way it is held on the object stage 5; very stable, closed design; tubular feed or removal tunnel for series objects; and the exclusion of any contamination influences.

Figure 10:
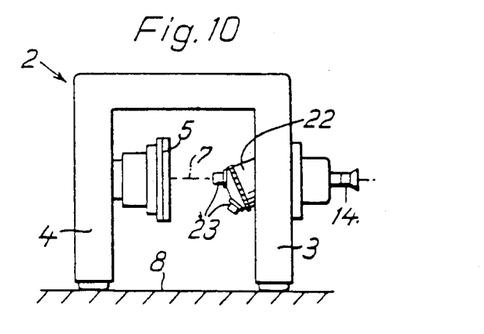
FIGS. 10-14 show highly schematicized side views of open vertical-frame stand designs with differing geometry of the frame longitudinal section, differing position of the particular object stage plane and also differing position of the frame "opening"
Figure 11:
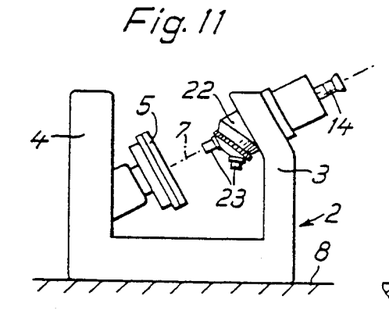
Figure 12:
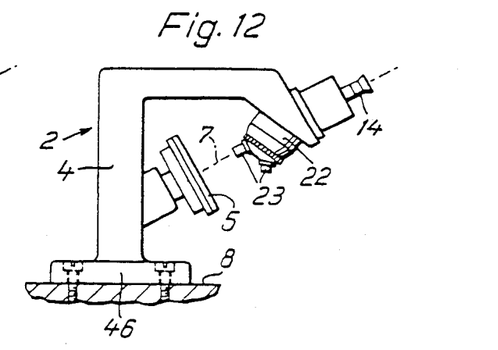
Figure 13:
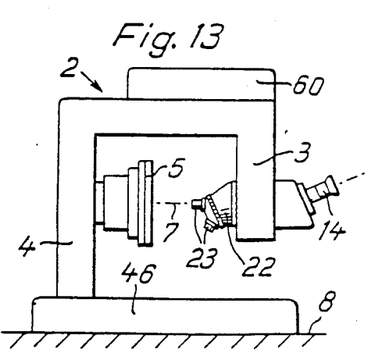
Figure 14:
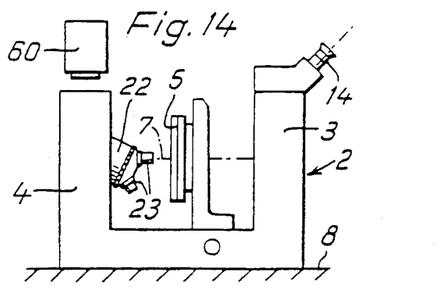

In FIGS. 10 to 14, "open" vertical-frame stand designs of differing frame longitudinal section geometry, differing orientation of the object stage plane in each case and also differing orientation of the frame "aperture" are represented. Here also, that which was stated above in the description of the "closed" frame stand versions applies in principle to the arrangement of the optical components or the possibilities of attachment of modules or the orientation of the optical axis 7 and therefore the object stage 5, and also regarding the air flow conditions. In FIG. 10, a design is specified having a frame aperture facing the horizontal mounting surface 8. Air flow apertures 48 or air suction apertures 49 can again be provided in the roof region of this stand. Light sources, not shown, for oblique reflected-light illumination of the particular object can also be provided. Furthermore, it is also possible for the object stage 5 to be mounted—as shown in FIG. 8, for example—rigidly on the horizontal mounting surface 8 and for the mobile instrument 2 to be positioned over the vertically mounted object stage 5. With a frame stand 2 extended in extreme fashion, transversely to the optical axis 7, in the fashion of that which is represented in FIG. 20, and with a successively arranged conveyor belt train having a plurality of vertical object holders which are moved in sequence into the microexamination position, the embodiment represented can more or less serve as an inspection terminal within a closed wafer transport line.

Figure 15:
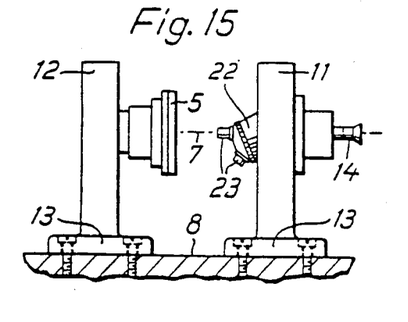
FIGS. 15 and 16 show highly schematicized side views of vertical single-stand combinations having differing position of the object stage plane.
Figure 16:
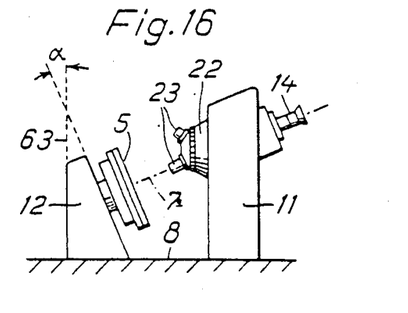

FIGS. 15 and 16 show side views of vertical singlestand combinations having differing orientation of the object stage plane.

Figure 17:
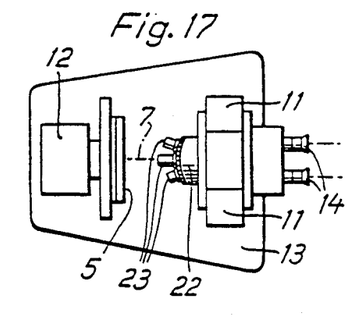
FIGS. 17-19 show highly schematicized plan views of vertical stand or single wall combinations.
Figure 18:
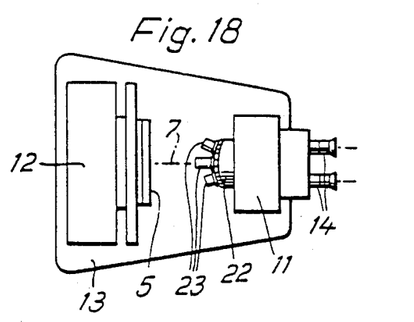
Figure 19:
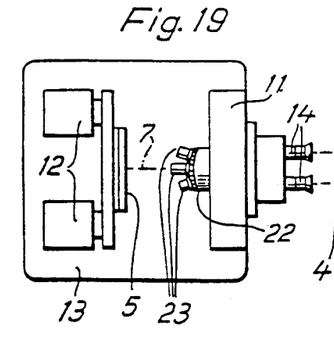

Finally, highly schematicized plan views of vertical stand or single-wall combinations are shown in FIGS. 17 to 19. In FIG. 17, the device comprises two front single-stand parts 11 which together carry the actual observation system, comprising an eyepiece unit and an objective unit. In FIG. 18, the rear stand part 12 is widened as a vertical wall. Alternative configurations include a portal, circular bow, angular bow and the like. Of course, more than two front or rear single-stand parts 11 or 12 could also be provided and equipped by means of a stand base plate 13 and/or a stand cover plate, not shown. In addition, the possibility arises of providing more than one binocular housing—for example, in the fashion of a multidiscussion bridge—or more than one object stage—for example, in the fashion of a comparison microscope.

By means of the described embodiments according to the invention, an optical observation instrument is specified with which contamination-free handling, inspection and measurement of high-precision, damage-sensitive objects, particularly large-surface-area wafers, is made possible in an ideal fashion. The instrument construction is stable, increased mechanical stage movement ranges are possible, the observer is presented with an ergonomic system having clear operation possibilities which do not affect the sensitive object region; the device can be upgraded for all special-purpose examination and measuring techniques known in microscopy; automation and remote control of all operational functions can be achieved, and similarly full operatability is possible during manual operation, while retaining all the mentioned advantages; objects with any dimensions are suitable for examination; laminar flow in the region of the object ensures freedom from dust; and the entire instrument has a low space requirement.

Reference number list

1—Frame stand (closed design)
2—Frame stand (open design)
3—Front frame stand part
4—Rear frame stand part
5—Object stage (rotatable mechanical stage)
6—Object (wafer)
7—Object-side section of the optical axis of the microscope
8—Horizontal mounting surface for the microscope casing
9—Vertical stop surface for the microscope casing
11—Front (single) stand part (front)(single) stand parts)
12—Rear (single) stand part (rear (single) stand parts)
13—Stand base plate
14—Eyepiece (binocular)
15—Deflection spitter prism
16—Photo connector
17—Deflection prism
18—Tube lens
19—Beam-splitter cube
20—Beam-splitter surface
21—Analyzer
22—Objective revolving nosepiece
23—Objectives
24—Field diaphragm
25—Hinged mirror (reflected-light or transmitted-light illumination)
26—Lamphousing
27—Light source
28—Reflected-light illumination optic
29—Reflected-light illumination beam path
30—Deflection element (hinged mirror)
31—Flanging surface for (reflected light) lamphousing
32—Deflection element
33—Reflected-light illumination optic
34—Polarizer (interference contrast device)
35—Full-wave plate
36—Autofocus system
37—Diaphragms
38—Tube lens
39—Optic
40—Length or angle measuring system
41—Optic
42—Intensity or spectral measuring instrument
43—Transmitted-light illumination optic
44—Transmitted-light illumination beam path
45—Console
46—Base plate of the frame stand (1)
47—Observer
48—Air flow apertures
49—Air suction apertures
50—Tube for air outlet aperture (or inlet aperture)
51—Double arrow (axial movement of the mechanical stage)
52—Rotary arrow (mechanical stage rotation)
53—Vacuum tube for upper object stage
54—Vacuum channels in upper object stage
55—(Vertical) control panel
56—Rotary arrow (mechanical stage rotation or combined mechanical stage/frame stand rotation)
57—Ball bearing-mounted linear guidance of the frame stand (1)
58—Double arrow (translation directions)
59—Fixed separate holder for object stage (5)
60—Attachment module
61—Observation module (eyepiece and objective unit)
62—Center of rotation of the system
63—Trace of that vertical plane which is perpendicular to the plane of the drawing (the vertical plane of the frame stand is in the plane of the drawing)
α—Angle between the trace of the object stage plane and the trace of an imaginary vertical plane
64,65—Rotary arrows which indicate the common opposed tilting of the components ($\alpha - 0°$)
66—Hollow section frame stand having trapezoidal cross section
67—Hollow cylinder (frame) stand
68—Object stage holder

I claim:

1. A transmitted-light or reflected-light microscope, wherein:
   (a) the microscope has a casing which comprises a frame stand in open or closed design having—from the view of the observer—a base, a front frame stand part and a rear frame stand part;
   (b) an object stage for receiving or holding objects to be viewed, is located between the front and the rear frame stand parts;
   (c) the portion of the microscope's optical axis oriented toward objects to be viewed lies perpendicular to the object stage plane and forms a discrete angle α, between 0° and 30° with the horizontal, and
   (d) a plurality of air openings are arranged in the upper region of the frame stand base or the lower region of a stand cover plate, and said openings are in communication with means for establishing a flow of room air therethrough.

2. A microscope as claimed in claim 1, wherein the stand parts or the frame stand parts form a discrete angle between 0° and 30° with the vertical.

3. A microscope as claimed in claim 1, wherein the object stage is mounted on the stand base plate or on the corresponding frame stand part.

4. A microscope as claimed in claim 1, wherein the object stage is connected rigidly to a horizontal microscope mounting surface and the frame stand is mounted so that it is movable axially relative to the object stage.

5. A transmitted-light or reflected-light microscope, wherein:
   (a) the microscope has a casing which comprises a base and at least two stand parts, which—preferably—are connected together by at least one common stand plate;
   (b) the stand parts are located—as seen from the observer—one behind the other;
   (c) an object stage for receiving or holding objects to be viewed is located between the front and the rear stand parts;
   (d) the portion of the microscope's optical axis oriented toward objects to be viewed lies perpendicular to the object stage plane and forms a discrete angle α, between 0° and 30° with the horizontal, and
   (e) a plurality of air openings are arranged in the upper region of the microscope base or in mutually facing portions of the stand parts, and said openings are in communication with means for establishing a flow of room air therethrough.

6. A microscope as claimed in claim 5, wherein the frame parts (11; 12) are constructed as stand columns (FIGS. 15 and 16).

7. A microscope as claimed in claim 6, wherein at least two front or at least two rear stand columns are provided.

8. A microscope as claimed in claim 5, wherein the stand parts (11; 12) are constructed as a stand wall or as stand walls.

9. A microscope as claimed in claim 5, wherein the stand parts (11; 12) are constructed as circular or angled bows.

10. A microscope as claimed in claim 5, wherein the optical elements for beam guidance and beam control are accommodated in the stand parts, in the stand base plate and in the stand cover plate or in the frame stand.

11. A microscope as claimed in claim 5, wherein the optical axis of the microscope is determined by an eyepiece system attached on the observer side to the front stand part or to the rear frame stand part and by an objective system provided, on the object side, on the front stand part or on the front stand part and also by a condenser system provided in the rear stand part or frame stand part.

12. A microscope as claimed in claim 5, wherein optical, mechanical and electronic control elements are arranged in the part of the stand base plate on the observer side or on the front stand part or on the rear frame part.

13. A microscope as claimed in claim 5, wherein at least one of the front stand part and the rear stand part is provided with at least one mount for interchangeably attaching illumination, observation, measuring or recording modules.

14. A microscope as claimed in claim 5, wherein the rear frame stand part or the rear stand part is provided with means for attachment of at least one external lamp housing.

15. A microscope as claimed in claim 5, wherein the object stage is constructed as a rotating mechanical stage, and means are provided for holding an object to be viewed on the object stage.

16. A microscope as claimed in claim 5, wherein the object stage is provided with suction holding devices.

17. A microscope as claimed in claim 5, wherein the object stage (5) is mounted on the rear frame stand part (4) or on the rear stand part (12).

18. A microscope as claimed in claim 5, wherein the frame stand (1; 2) possesses a rectangular or quadratic longitudinal section and the base plate (46) is extended on the observer side and is constructed as a manual console (45) (FIG. 1, 2 or 4).

19. A microscope as claimed in claim 5, wherein the frame stand (1; 2) possesses a trapezoidal or parallelogram-shaped longitudinal section with an inclined frame front part (3) which faces the observer (47) (FIGS. 5, 6, 11 and 12).

20. A microscope as claimed in claim 19, wherein the frame stand part (3), on the observer side, and the object stage (5) are arranged in planes which are parallel to one another.

21. A microscope as claimed in claim 5 wherein the casing is a—at least partially double-walled—hollow section element (66) which is extended longitudinally, transversely to the optical axis, according to the particular geometry of the frame longitudinal section (FIG. 20).

22. A microscope as claimed in claim 5, wherein the microscope casing comprises a hollow cylinder (67) having a circular cross section, the object stage (5), on the one hand, and also the modular eyepiece and objective unit (61), on the other hand, being mounted on circularly arcuate translation segments so as to be movable (64, 65) in a diametrically opposed fashion for the setting of a discrete angle α, between 0° and 30°, relative to the inclination of the object stage plane to the vertical plane (63) (FIG. 9).

23. A microscope as claimed in claim 5, wherein means are provided on the stand part or frame part for attachment and coupling of special-purpose microscope modules 24. A microscope as claimed in claim 5, wherein said microscope is located in an atmospherically closed system and is fitted with means for remote control of microscope operation and control functions 25. A microscope as claimed in claim 5, wherein the object (6) is subjected to a specifically adjustable laminar air or protective gas stream (48–50).

26. The use of a microscope as claimed in claim 5 as a wafer inspection and measurement device.

27. The use of a microscope as claimed in claim 5 as an integrated instrument within a wafer production and control line.

28. A microscope wherein
(a) the microscope has a casing which comprises a frame stand in open or closed design having—from the view of the observer—a base, a front stand part and a rear frame stand part;
(b) an object stage for receiving or holding objects to be viewed is located between the front and the rear frame stand parts;
(c) the portion of the microscope's optical axis oriented toward objects to be viewed lies perpendicular to the object stage plane and forms a discrete angle α, between 0° and 30° with the horizontal, and
(d) the frame stand is mounted so that it can rotate about the microscope's optical axis, which extends horizontally.

29. A microscope as claimed in claim 28, wherein the object stage is mounted on a vertical wall and follows the rotational movement of the frame stand.

30. A microscope as claimed in claim 28, wherein the object stage is axially movable and is mounted so that it cannot rotate.

* * * * *